United States Patent [19]

Eguchi et al.

[11] Patent Number: 5,008,469

[45] Date of Patent: Apr. 16, 1991

[54] PROCESS FOR PRODUCING TETRABROMOBISPHENOL A

[75] Inventors: Hisao Eguchi; Masashige Kubo; Koji Kunimoto, all of Tokuyama; Sadami Shimizu, Tokyo; Masakatsu Sato, Matsudo; Hanzo Tamabayashi, Tokuyama, all of Japan

[73] Assignee: Tosoh Corporation, Shinnanyo, Japan

[21] Appl. No.: 470,212

[22] Filed: Jan. 25, 1990

[30] Foreign Application Priority Data

| Jan. 26, 1989 | [JP] | Japan | 1-15066 |
| Jan. 27, 1989 | [JP] | Japan | 1-16296 |
| Dec. 20, 1989 | [JP] | Japan | 1-328168 |
| Jan. 11, 1990 | [JP] | Japan | 2-2576 |

[51] Int. Cl.$^5$ .................. C07C 39/367; C07C 37/18

[52] U.S. Cl. ..................................... 568/722; 568/723
[58] Field of Search ............... 568/722, 726, 723, 728

[56] References Cited

FOREIGN PATENT DOCUMENTS

| 686772 | 5/1964 | Canada | 568/722 |
| 706433 | 3/1965 | Canada | 568/722 |
| 341790 | 7/1972 | U.S.S.R. | 568/722 |

Primary Examiner—Werren B. Lone
Attorney, Agent, or Firm—Oblon, Spivak, McClelland, Maier & Neustadt

[57] ABSTRACT

A process for producing tetrabromobisphenol A, which comprises brominating bisphenol A in methanol, wherein the substrate concentration of bisphenol A to methanol is at most 20 wt/vol %.

9 Claims, No Drawings

PROCESS FOR PRODUCING TETRABROMOBISPHENOL A

The present invention relates to a process for producing tetrabromobisphenol A (hereinafter referred to simply as TBA). TBA is a compound useful as a reactive-type flame retardant for epoxy laminates or as an additive-type flame retardant for general purpose resins such as ABS. Resins having flame retardancy imparted by TBA are used mainly for peripheral parts or housings of electrical products, to which high voltages are to be applied.

TBA is produced usually by the reaction of bisphenol A (hereinafter referred to simply as BPA) and bromine in an organic solvent such as a lower alkyl alcohol or a halogenated hydrocarbon. For the industrial purpose, methanol is usually selected as the solvent for reaction, since formation of impurities is thereby relatively small. When methanol is employed as the solvent for reaction, hydrogen bromide formed by the bromination reaction of BPA reacts with the methanol to form methyl bromide. This methyl bromide is a useful substance, for example, as fumigant for agricultural chemicals. Therefore, in the conventional industrial process for the production of TBA, it has been common to produce TBA and methyl bromide simultaneously. However, due to a decrease in the demand for agricultural chemicals in recent years, the balance in the demand of the two products has been broken, and it is now desired to develop a process for producing TBA alone without producing methyl bromide. Further, methyl bromide is a substance having high toxicity. It is very important to suppress the formation of methyl bromide not only for the improvement of the recovery rate of methanol and hydrogen bromide after the reaction but also from the viewpoint of working environment and safety.

As a method for suppressing the formation of methyl bromide, Japanese Examined Patent Publication No. 3376/1966 proposes a method wherein water is added to the reaction system. However, this method requires a high temperature to complete the bromination reaction and thus has problems such as decomposition of TBA and undesirable side reactions such as bromination of the side chain alkyl groups.

Japanese Examined Patent Publication No. 204947/1978 proposes a method wherein chlorine is added to the reaction system, and hydrogen bromide is recovered as a bromine source thereby to control the formation of methyl bromide. However, this method has a problem that a chlorination reaction takes place simultaneously, whereby the purity of the product tends to be poor.

Further, TBA crystals obtained by the above-mentioned conventional methods usually contain from about 100 to 2,000 ppm of a hydrolyzable bromide and from about 20 to 100 ppm of inorganic bromine ions.

TBA is used in a large amount as a reactive-type flame retardant for epoxy resin compositions. It is formulated in the form of TBA alone or in the form of an epoxy resin having TBA as a backbone. However, in such use for epoxy resins, there is a problem that the hydrolyzable bromide and inorganic bromine ions contained in TBA adversely affect the curing reaction of the resins or the resin properties after the curing. Especially in the case of epoxy resins for electrical or electronic materials such as laminates or encapsulating agents, their presence creates a serious problem.

Namely, when TBA having a large hydrolyzable bromide content is used for an epoxy resin for an electrical or electronic material, such impurities tend to be liberated as bromine ions due to e.g. moisture, and the liberated bromine ions bring about corrosion of metals, thus impairing the reliability of the material.

Accordingly, TBA to be used for such applications, is required to be purified by e.g. recrystallization to reduce the hydrolyzable bromide and inorganic bromine ion content. Japanese Unexamined Patent Publication No. 3139/1989 proposes, as an especially effective purification method, a method for treating TBA by contacting TBA dissolved under heating in an aromatic hydrocarbon, with an aqueous alkali metal solution. However, even when this purification method is carried out, the resulting TBA still contains from 50 to 100 ppm of the hydrolyzable bromide, and as such, it is not necessarily satisfactory for application to electrical or electronic materials. Further, this method requires a special purification step, and it is cumbersome and non-economical from the industrial point of view.

On the other hand, the method of brominating BPA in methanol has a problem that from 2 to 5% by weight, based on formed TBA, of dibromobisphenol A and tribromobisphenol A are usually dissolved in the filtrate after precipitation of TBA, and they tend to cause a decrease of the yield of the product or the deposition of scales to the apparatus during the recovery of methanol.

It is an object of the present invention to provide a process for producing TBA alone without impairing the quality of TBA while suppressing the formation of methyl bromide as by-product.

A further object is to provide a process for producing high quality TBA with the hydrolyzable bromide and inorganic bromine ions remarkably reduced to such an extent that could not be accomplished by the conventional methods.

Another object is to provide an industrial process which is economically advantageous and which is a simplification of the conventional process which required cumbersome process steps and was economically disadvantageous.

For the purpose of the present invention, the hydrolyzable bromide is represented by the amount of bromine ions dissociated when TBA is dissolved in a potassium hydroxide-methanol solution and refluxed for 15 minutes, as represented by the weight ratio to TBA. Likewise, the inorganic bromine ions are represented by the amount of bromine ions freed when TBA is dissolved in acetone, as represented by the weight ratio to TBA.

The quantitative analysis of the amounts of such bromine ions can be conducted by e.g. a potentiometric titration method by means of an aqueous silver nitrate solution, or by ion liquid chromatography.

The present inventors have conducted extensive studies to solve the above-mentioned problems of the conventional techniques and as a result, have found it possible to control the formation of methyl bromide by adjusting the substrate concentration of BPA to methanol at a level of at most 20 wt/vol% and conducting the bromination reaction at a temperature of not higher than 25° C. in the process for brominating BPA with bromine in methanol. Further, it has been found surprisingly that when the substrate concentration of BPA to methanol is adjusted at a level of from 0.1 to 10 wt/vol%, high quality of TBA having the hydrolyzable bromide and inorganic bromine ions remarkably reduced as compared with the conventional method conducted at a substrate concentration of from about 15 to 57 wt/vol%, can be obtained. Further, in the process of the present invention, it has been made possible to recover and reuse substantially quantitatively dibromobisphenol A and tribromobisphenol A as precursors, by adding an organic solvent inert to the bromination reaction and insoluble in water, such as chlorobenzene, in an amount of from 1 to 8% by weight to the methanol. Furthermore, it has been found possible to control the formation of methyl bromide by using a methanol containing from 5 to 15% by weight of water as a solvent in the process for brominating BPA with bromine, and thereby to obtain high quality TBA having the hydrolyzable bromide and inorganic bromine ions remarkably reduced, in good yield. The present invention has been accomplished on the basis of these discoveries.

The present invention provides a process for producing tetrabromobisphenol A, which comprises brominating bisphenol A in methanol, wherein the substrate concentration of bisphenol A to methanol is at most 20 wt/vol%.

The present invention also provide a process a process for producing tetrabromobisphenol A which comprises brominating bisphenol A in methanol, wherein the bromination is conducted at a temperature of not higher than 25° C.

Further, the present invention provides a process for producing tetrabromobisphenol A which comprises brominating bisphenol A in methanol, wherein the substrate concentration of bisphenol A to methanol is at most 20 wt/vol%, and the bromination is conducted at a temperature of not higher than 25° C.

Furthermore, the present invention provides a process for producing tetrabromobisphenol A which comprises brominating bisphenol A in methanol, wherein at least one organic solvent inert to the bromination reaction and insoluble in water is added to methanol in an amount of from 1 to 8% based on the methanol.

A still further, the present invention provides a process for producing tetrabromobisphenol A which comprises brominating bisphenol A with bromine, wherein methanol containing from 5 to 15% by weight of water is used as the solvent for reaction, so that a hydrolyzable bromide and inorganic bromine ions are minimized.

Now, the present invention will be described in detail with reference to the preferred embodiments.

Firstly, in a process of the present invention, the substrate concentration of BPA to methanol is adjusted to a level of at most 20 wt/vol% and the bromination reaction is conducted at a temperature of not higher than 25° C., whereby formation of methyl bromide can be suppressed.

For example, if the reaction temperature is 30° C., methyl bromide is produced in an amount of from 4.5 mol% per formed hydrogen bromide. Whereas, by lowering the reaction temperature to 20° C., the amount of methyl bromide produced as a by-product can be reduced to 1/4 or less. Further, the amount of methyl bromide can be reduced to a level of 1/10 or less by lowering the reaction temperature to 5° C. On the other hand, when the substrate concentration to methanol is 23 wt/vol%, the amount of methyl bromide formed as a by-product is 2.5 mol% per formed hydrogen bromide. By diluting the solution to a substrate concentration of 13 wt/vol%, the amount of methyl bromide formed can be reduced to a level of 1/2 or less.

Further, it is possible to obtain high quality TBA having the hydrolyzable bromide and inorganic bromine ions remarkably reduced, by adjusting the substrate concentration of BPA to methanol to a level of from 0.1 to 10 wt/vol% in the process of the present invention.

In a process for producing TBA by brominating BPA with bromine in methanol, hydrogen bromide produced as a by-product in the reaction system gives a substantial influence over the reaction rate of the bromination.

Namely, in such a high substration concentration region (from 15 to 57 wt/vol%) as disclosed in the above-mentioned mentioned prior art, a large amount of hydrogen bromide will accumulate in the reaction solvent, whereby the reaction rate of the bromination will be extremely reduced. This may be explained in such a manner that the accumulated hydrogen bromide hinders the dissociation of hydroxyl groups of BPA and the electron density of the aromatic ring of BPA decreases, whereby the reaction with bromine cations is thereby suppressed. Therefore, the reaction at such a high substrate concentration region, usually requires a high reaction temperature.

On the other hand, in a low substrate concentration region as in the process of the present invention, hydrogen bromide accumulated in the reaction solvent is in a small amount, whereby there will be no reduction in the reaction rate.

The hydrolyzable bromide is believed to be derived from an alkyl bromide having a relatively weak carbon-bromine bond formed by the bromination of impurities in BPA and/or by bromination of side chain alkyl groups of TBA. Further, this alkyl bromide is believed to be formed primarily by the reaction with bromine radicals.

The reason for the reduction of the hydrolyzable bromide content when the substrate concentration of BPA to methanol was adjusted to a level of from 0.1 to 10 wt/vol%, is not necessarily clearly understood. However, it is believed that in such a lower substrate concentration region, formation of bromine radicals is suppressed, and formation of the alkyl bromide which brings about the hydrolyzable bromide, is also suppressed. Namely, in a low substrate concentration region as in the present invention, the reaction of BPA with bromine cations is quick as mentioned above, and consequently, formation of bromine radicals is believed to be suppressed. Further, in the process of the present invention, the hydrogen bromide concentration in the reaction solvent is low, whereby the content of inorganic bromine ions is believed to be likewise reduced.

When the process for brominating BPA in methanol is to be carried out, the substrate concentration of BPA is at most 20 wt/vol%, preferably from 0.1 to 10 wt/vol%. If the concentration exceeds 20 wt/vol%, the amount of methyl bromide formed as a by-product increases, such being undesirable. When the substrate concentration is adjusted at a level of from 0.1 to 10 wt/vol%, it is possible to obtain high quality TBA having the hydrolyzable bromide and inorganic bromine ions remarkably reduced.

In the process of the present invention, bromine is used in an amount of from 4.0 to 5.0 mols, preferably from 4.1 to 4.5 mols, per mol of BPA. If the molar ratio is less than 4.0, the yield of TBA tends to be low, and if it exceeds 5.0, a side-reaction due to excess bromine is likely to take place, such being undesirable.

Usually, bromine is gradually added over a period of from 0.5 to 10 hours. The reaction temperature during the addition of bromine is from about 10° to 50° C., particularly preferably from about 10° to 25° C. If the temperature is lower than 0° C., the reaction rate tends to be substantially slow, and if it exceeds 50° C., a side-reaction such as decomposition of TBA is likely to take place, such being undesirable. When the addition of bromine is conducted at a temperature of not higher than 25° C., formation of methyl bromide as a by-product can be suppressed.

After completion of the addition of bromine, it is usual to conduct aging for a period of from 0.5 to 5 hours to complete the reaction. There is no particular restriction as to the reaction temperature during the aging. However, it is usual to employ a temperature of from 10° to 25° C. taking the reduction of methyl bromide into consideration.

After completion of the reaction, water is added to the reaction solution to precipitate TBA dissolved in the reaction solution. The amount of water to be added is usually from about 30 to 100% by weight based on the solvent for reaction. If the amount is less than 30% by weight, the amount of precipitated TBA will be small, and if it exceeds 100% by weight, the purity of TBA tends to be reduced, such being undesirable.

In the process of the present invention, TBA crystals are separated from the reaction solution by filtration, then washed with water and dried to obtain a product.

In the filtrate obtained in the above process, dibromobisphenol A and tribromobisphenol A are usually dissolved in an amount of from 2 to 5% by weight based on formed TBA, and they cause a decrease of the yield of the product or adhesion of scales to the apparatus during the recovery of methanol.

In the process of the present invention, dibromobisphenol A and tribromobisphenol A as the precursors, can be recovered and recycled almost quantitatively, by adding an inorganic solvent inert to the bromination reaction and insoluble in water, such as chlorobenzene, in an amount of from 1 to 8% by weight, based on the methanol.

Namely, such a water-insoluble organic solvent is added to methanol, and TBA and the filtrate are obtained by a usual method. Then, water is added in an amount sufficient to bring about phase separation of the organic solvent added to the filtrate, so that bromobisphenols dissolved in the filtrate can be extracted to the organic solvent layer, and this organic solvent layer is returned to the reaction system, whereby by-product bromobisphenols can be almost completely be recovered. These compounds returned to the reaction system, will further be brominated to TBA. Consequently, the yield of TBA can substantially be improved. Further, in the filtrate after the separation and recovery of such bromobisphenols, no substantial amount of high boiling point components exist whereby such a trouble as the deposition of scales during the recovery of methanol or in other steps, can substantially be reduced. When it is required to completely remove high boiling point substances which may be remain in a trace amount in the filtrate, it is advisable to repeat once again the extraction treatment of the filtrate with a pure organic solvent.

The organic solvent added at the initial stage, is recycled together with bromobisphenols, whereby it is not substantially consumed, and it may be supplemented only from time to time.

Any solvent may be used as the organic solvent, so long as it is inert to the bromination reaction and insoluble in water and capable of dissolving brominated bisphenols. For example, chlorobenzene, benzene and 1,1,2-trichloroethane are particularly suitable.

The amount of the organic solvent to be added to the methanol solvent, is usually from 1 to 8% by weight, preferably from 3 to 5% by weight, based on the methanol. If the amount is less than 1% by weight, the extraction efficiency of the brominated bisphenols in the filtrate and the state of phase separation tend to become worse, and if the amount exceeds 8% by weight, the solvent tends to dissolve the TBA product during the crystallization step. Thus, in either case, the yield of TBA will decrease.

It is conceivable to employ a method in which the solvent for extraction is not preliminarily added to the methanol solvent, and instead, low brominated bisphenols are extracted from the filtrate with a fresh solvent, and then the solvent is separated by distillation so that only the brominated bisphenols are returned to the reaction system. However, dibromobisphenol A and tribromobisphenol A as the main components of the brominated bisphenols are highly adhesive, and there will be a serious problem for their transportation. Further, the distillation of the solvent adds to the energy cost.

Further, by using methanol containing from 5 to 15% by weight of water as a solvent for reaction in the process for producing TBA, it is possible to produce high quality TBA having the hydrolyzable bromide and bromine ions substantially reduced.

The hydrolyzable bromide is believed to be derived from an alkyl bromide having a relatively weak carbon-bromine bond formed by the bromination of impurities in BPA and/or by the bromination of side chain alkyl groups of TBA.

The reason for the reduction of the hydrolyzable bromide when methanol containing from 5 to 15% by weight of water, is used as the solvent for reaction, is not necessarily clearly understood. However, it is considered that the addition of water serves to suppress formation of bromine radicals, whereby formation of an alkyl bromide which brings about the hydrolyzable bromide, is suppressed. Namely, by the addition of water, the dissociation of hydroxyl groups of BPA is promoted, and the reactivity with bromine cations is increased. Consequently, formation of bromine radicals is thereby suppressed. Further, in the process of the present invention, resulting TBA gradually precipitates during the reaction, whereby inclusion of inorganic bromine ions will thereby be suppressed.

$$CH_3OH + HBr \rightleftarrows CH_3Br + H_2O$$

On the other hand, the reason for the substantial reduction in the amount of methyl bromide formed, is believed to be such that as shown by the above reaction formula, the reaction for forming methyl bromide is an equilibrium reaction accompanying formation of water, and accordingly, the equilibrium is returned to the initial system by the addition of water.

The solvent for reaction to be used in the process of the present invention is methanol containing from 5 to 15% by weight of water. Preferably, methanol containing from 7 to 12% by weight of water is selected. If the water content is less than 5% by weight, no adequate effect for reducing the hydrolyzable bromide will be obtained, and if the water content exceeds 15% by weight, there will be a deterioration in the purity or coloring of resulting TBA, such being undesirable. There is no particular restriction as to the substrate concentration of BPA in the solvent for reaction. However, the reaction is usually conducted at a substrate concentration of from 5 to 30% by weight.

The amount of bromine to be used for the process of the present invention is from 4.0 to 5.0 (by molar ratio), preferably from 4.1 to 4.5 (by molar ratio), to BPA. If the molar ratio is less than 4.0, the yield of TBA tends to be low, and if it exceeds 5.0, a side-reaction is likely to take place due to excess bromine, such being undesirable.

Bromine is usually added gradually over a period of from 0.5 to 10 hours. The reaction temperature during the addition of bromine is from about 0° to 50° C., preferably from about 10° to 30° C. If the reaction temperature is less than 0° C., the reaction rate tends to be extremely slow, and if it exceeds 50° C., a side-reaction such as decomposition of TBA is likely to take place, such being undesirable.

After completion of the addition of bromine, aging for a period of from 0.5 to 5 hours is usually conducted to complete the reaction. There is no particular restriction as to the reaction temperature during the aging. However, the temperature is selected usually within a range of from about 10° to 40° C. taking the formation of methyl bromide into consideration.

In the process of the present invention, resulting TBA gradually precipitates as crystals during the reaction. Accordingly, the reaction solution after the reaction, will be a slurry containing TBA crystals. The TBA crystals contained in this reaction solution constitute from about 45 to 85% by weight of the formed TBA.

After completion of the reaction, water is added to the reaction solution to precipitate TBA dissolved in the reaction solution. The amount of water to be added, is usually from about 30 to 100% by weight to the solvent for reaction. If the amount is less than 30% by weight, precipitation of TBA tends to be small, and if it exceeds 100% by weight, the purity of TBA tends to deteriorate, such being undesirable.

In the process of the present invention, TBA crystals are separated from the reaction solution by filtration, then washed with water and dried to obtain a product. TBA obtained by the process of the present invention, is TBA of high quality containing as little as from 5 to 50 ppm of the hydrolyzable bromide and from 0 to 15 ppm of inorganic bromine ions.

As is evident from the foregoing description, according to the present invention, formation of methyl bromide as a by-product can be suppressed, and it is possible to produce high quality TBA having the hydrolyzable bromide and inorganic bromine ions remarkably reduced, which has never been accomplished by the conventional methods.

Accordingly, TBA obtained by the process of the present invention, requires no particular purification step and may per se be used as a flame retardant for resins useful for electrical and electronic materials such as laminates or encapsulating agents.

Further, by adding an organic solvent inert to the bromination reaction and insoluble in water, such as chlorobenzene, in an amount of from 1 to 8% by weight to methanol in the process of the present invention, it is possible to recover and recycle dibromobisphenol A and tribromobisphenol A as precursors, almost quantitatively, and it is thereby possible to substantially increase the yield of TBA.

Thus, by the process of the present invention, high purity TBA can be produced industrially advantageously and safely by simplifying the conventional processes.

Now, the present invention will be described in further detail with reference to Examples. However, it should be understood that the present invention is by no means restricted to such specific Examples.

EXAMPLES 1 and 2 and COMPARATIVE EXAMPLES 1 and 2

57 g (0.4 mol) of bisphenol A was dissolved in a predetermined amount of methanol. This solution was cooled to a temperature as identified in Table 1, and while maintaining this temperature, 164.8 g (1.03 mols) of bromine was dropwise added to the surface of the solution over a period of 3 hours under stirring. Thereafter, the solution was stirred for further 3 hours. Then, deionized water was dropwise added thereto to precipitate crystals of tetrabromobisphenol A, followed by filtration. Hydrogen bromide in the filtrate was neutralized, and then methyl bromide was taken out by distillation and its weight was measured. The results thus obtained are shown in Table 1.

For the purpose of comparison, the reaction was conducted under the conditions as identified in Table 1, and the results are also shown in Table 1.

TABLE 1

|  | Methanol (ml) | BPA/ methanol (wt/vol %) | Reaction temp. (°C.) | Amount of methyl bromides (g) |
| --- | --- | --- | --- | --- |
| Example 1 | 425 | 13.4 | 20 | 1.1 |
| Example 2 | 425 | 13.4 | 5 | 0.4 |
| Comparative Example 1 | 425 | 13.4 | 30 | 4.5 |
| Comparative Example 2 | 253 | 22.5 | 20 | 2.4 |

EXAMPLE 3

Into a four-necked flask equipped with a thermometer, a stirrer and a condenser, 18.3 g (80 mmol) of BPA was charged, and 700 ml of methanol was added thereto to dissolve BPA.

Then, while maintaining the reaction solution at 20° C., 54.3 g (340 mmol) of bromine was dropwise added thereto over a period of 3 hours. Thereafter, aging was conducted at the same temperature for further 2 hours.

After aging, remaining excess bromine was reduced by an addition of an aqueous hydrazine solution. Then, water (420 ml) was added to the reaction solution to precipitate TBA dissolved in the solution.

Then, precipitated crystals were collected by filtration, washed with water and dried to obtain 42.3 g of TBA as white crystals.

The isolated TBA crystals were analyzed by high performance liquid chromatography, whereby the purity of crystals was found to be 99.9%. Further, the crystals were subjected to potentiometric titration by means of an aqueous silver nitrate solution, whereby they were found to contain 13 ppm of a hydrolyzable bromide and 1 ppm of inorganic bromine ions.

The reaction conditions are shown in Table 2, and the results of the reaction are shown in Table 3.

EXAMPLES 3 to 8

The operation was conducted in the same manner as in Example 3 except that the reaction conditions were as identified in Table 2. The results of the reaction are shown in Table 3.

COMPARATIVE EXAMPLES 3 to 6

The operation was conducted in the same manner as in Example 3 except that the reaction conditions were as identified in Table 2. The results of the reaction are shown in Table 3.

TABLE 2

|  | Charge | | Reaction | | Precipitation |
|---|---|---|---|---|---|
|  | Methanol (ml) | BPA/ methanol (wt/vol %) | Temp. during the dropwise addition of bromine (°C.) | Temp. during aging (°C.) | Water for precipitation[1] (ml) |
| Example 3 | 700 | 2.6 | 20 | 20 | 420 |
| Example 4 | 350 | 5.2 | 20 | 20 | 210 |
| Example 5 | 250 | 7.3 | 10 | 20 | 150 |
| Example 6 | 250 | 7.3 | 20 | 20 | 150 |
| Example 7 | 250 | 7.3 | 20 | 40 | 150 |
| Example 8 | 185 | 9.9 | 20 | 20 | 111 |
| Comparative Example 3 | 150 | 12.2 | 20 | 20 | 90 |
| Comparative Example 4 | 100 | 18.3 | 20 | 20 | 60 |
| Comparative Example 5 | 70 | 26.1 | 20 | 20 | 42 |
| Comparative Example 6 | 70 | 26.1 | 20 | 40 | 42 |

[1]The ratio of water for precipitation to methanol was constant. Water for precipitation/methanol = 60 (vol %)

TABLE 3

|  | Results of the reaction | | | | |
|---|---|---|---|---|---|
|  | Amount (g) | Purity (wt. %) | Yield (mol %) | Hydrolyzable bromine (ppm) | Inorganic bromine ions (ppm) |
| Example 3 | 42.3 | 99.9 | 97.1 | 13 | 1 |
| Example 4 | 42.4 | 99.8 | 97.3 | 16 | 3 |
| Example 5 | 42.1 | 99.5 | 96.3 | 9 | 1 |
| Example 6 | 42.6 | 99.8 | 97.7 | 12 | 2 |
| Example 7 | 42.7 | 99.7 | 97.8 | 35 | 9 |
| Example 8 | 42.2 | 99.4 | 96.4 | 47 | 5 |
| Comparative Example 3 | 42.0 | 98.8 | 95.4 | 174 | 21 |
| Comparative Example 4 | 41.6 | 97.0 | 92.7 | 236 | 23 |
| Comparative Example 5 | 40.2 | 94.3 | 87.1 | 118 | 15 |
| Comparative Example 6 | 42.3 | 99.3 | 96.5 | 291 | 29 |

EXAMPLE 9

57 g of bisphenol A was dissolved in a solvent mixture comprising 336 g of methanol and 18 g of chlorobenzene. Then, 165 g of bromine was dropwise added thereto over a period of about 3 hours at a reaction temperature of 20° C. to conduct the bromination reaction. After completion of the reaction and aging, water necessary for crystallization was added to the reaction solution to precipitate TBA crystals. TBA was separated by filtration and then dried to obtain TBA having a purity of at least 99% in a yield of 97%. On the other hand, water was added to the filtrate for the phase separation of a chlorobenzene layer to obtain about 18 g of the chlorobenzene layer. The extraction rate of brominated bisphenols from the filtrate was 98%.

EXAMPLE 10

The chlorobenzene layer obtained in Example 9 was added to 336 g of methanol, and then bisphenol A was dissolved therein. Then, the reaction was conducted in the same manner as in Example 9 to obtain TBA having a purity of at least 99% in a yield of 99%. Further, by the phase separation from the filtrate, about 18 g of a chlorobenzene layer was obtained. The extraction rate of brominated bisphenols from the filtrate was 98%.

EXAMPLE 11

By repeating Example 10, the following results were obtained.

| Number of repetition | 2nd time | 3rd time | 4th time |
|---|---|---|---|
| Yield of TAB | 99% | 98.5% | 99% |
| Extraction rate of brominated bisphenols from the filtrate | 98% | 98.5% | 98.5% |

EXAMPLE 12

The operation was conducted in the same manner as in Example 9 except that the chlorobenzene was changed to 1,1,2-trichloroethane, and the following results were obtained.

| Yield of TBA | 96.5% |
|---|---|
| Extraction rate of brominated bisphenols | 99% |

EXAMPLE 13

The operation was conducted ian the same manner as in Example 10 except that the chlorobenzene was changed to 1,1,2-trichloroethane, and the following results were obtained.

| Yield of TBA | 99% |
|---|---|
| Extraction rate of | 98% |

-continued brominated bisphenols

EXAMPLE 14

Into a four-necked flask having a capacity of 300 ml and equipped with a thermometer, a stirrer and a condenser, 18.3 g (80 mmol) of BPA was charged, and 128 ml of methanol and 8 ml of water were added thereto to dissolve BPA.

Then, while maintaining the reaction solution at 20° C., 54.3 g (340 mmol) of bromine was dropwise added thereto over a period of 3 hours, and aging was conducted at the same temperature for further 2 hours. Here, the amount of methyl bromide in the reaction solution was quantitatively measured by gas chromatography, whereby the amount formed was found to be 0.43 g.

After aging, remaining excess bromine was reduced by an addition of an aqueous hydrazine solution. Then, water (74 ml) was added to the reaction solution to precipitate TBA dissolved in the solution.

Then, precipitated crystals were collected by filtration, washed with water and dried to obtain 42.6 g of TBA as white crystals.

The isolated TBA crystals were analyzed by high performance liquid chromatography, whereby the purity of the crystals were found to be 99.6%. Further, the crystals were subjected to potentiometric titration by means of an aqueous silver nitrate solution, whereby they were found to contain 15 ppm of a hydrolyzable bromide and 2 ppm of inorganic bromine ions.

The reaction conditions are shown in Table 4, and the results of the reaction are shown in Table 5.

EXAMPLES 15 to 21

The operation was conducted in the same manner as in Example 14 except that the reaction conditions were as identified in Table 4. The results of the reaction are shown in Table 5.

COMPARATIVE EXAMPLES 7 to 10

The operation was conducted in the same manner as in Example 14 except that the reaction conditions were as identified in Table 4. The results of the reaction are shown in Table 5.

COMPARATIVE EXAMPLE 11

Into a four-necked flask having a capacity of 300 ml and equipped with a thermometer, a stirrer and a condenser, 18.3 g (80 mmol) of BPA was charged, and 128 ml of ethanol and 8 ml of water were added thereto to dissolve BPA.

Then, while maintaining the reaction solution at 20° C., 54.3 g (340 mmol) of bromine was dropwise added thereto over a period of 3 hours, and aging was conducted at the same temperature for further 2 hours.

After aging, remaining excess bromine was reduced by an addition of an aqueous hydrazine solution. Then, water (74 ml) was added to the reaction solution to precipitate TBA dissolved in the solution.

Then, precipitated crystals were collected by filtration, washed with water and dried to obtain 42.8 g of TBA as white crystals.

The isolated TBA crystals were analyzed by high performance liquid chromatography, whereby the purity of the crystals were found to be 97.3%. Further, the crystals were subjected to potentiometric titration by means of an aqueous silver nitrate solution, whereby they were found to contain 288 ppm of a hydrolyzable bromide and 29 ppm of inorganic bromine ions.

COMPARATIVE EXAMPLE 12

Into a four-necked flask having a capacity of 300 ml and equipped with a thermometer, a stirrer and a condenser, 18.3 g (80 mmol) of BPA was charged, and 128 ml of n-butanol and 8 ml of water were added thereto to dissolve BPA.

Then, while maintaining the reaction solution at 20° C., 54.3 g (340 mmol) of bromine was dropwise added thereto over a period of 3 hours, and aging was conducted at the same temperature for further 2 hours.

After aging, remaining excess bromine was reduced by an addition of an aqueous hydrazine solution. Then, water (74 ml) was added to the reaction solution to precipitate TBA dissolved in the solution.

Then, precipitated crystals were collected by filtration, washed with water and dried to obtain 40.9 g of TBA as white crystals.

The isolated TBA crystals were analyzed by high performance liquid chromatography, whereby the purity of the crystals was found to be 94.7%. Further, the crystals were subjected to potentiometric titration by means of an aqueous silver nitrate solution, whereby they were found to contain 364 ppm of a hydrolyzable bromide and 35 ppm of inorganic bromine ions.

TABLE 4

| | Solvent for reaction | | | Reaction conditions | | |
| --- | --- | --- | --- | --- | --- | --- |
| | Methanol (ml) | Water (ml) | Water/ solvent (wt. %) | Temp. during the dropwise addition of bromine (°C.) | Temp. during aging (°C.) | Reaction solution (after aging) |
| Example 14 | 128 | 8 | 7.3 | 20 | 20 | Slurry |
| Example 15 | 125 | 11 | 10.0 | 10 | 20 | Slurry |
| Example 16 | 125 | 11 | 10.0 | 20 | 20 | Slurry |
| Example 17 | 125 | 11 | 10.0 | 20 | 40 | Slurry |
| Example 18 | 125 | 11 | 10.0 | 30 | 40 | Slurry |
| Example 19 | 122 | 14 | 12.7 | 20 | 20 | Slurry |
| Example 20 | 120 | 16 | 14.4 | 20 | 20 | Slurry |
| Example 21 | 120 | 16 | 14.4 | 20 | 40 | Slurry |
| Comparative Example 7 | 136 | 0 | 0 | 20 | 20 | Uniform solution |
| Comparative Example 8 | 136 | 0 | 0 | 20 | 40 | Uniform solution |
| Comparative Example 9 | 131 | 5 | 4.6 | 20 | 20 | Uniform solution |

TABLE 4-continued

|  | Solvent for reaction | | | Reaction conditions | | |
|---|---|---|---|---|---|---|
|  | Methanol (ml) | Water (ml) | Water/ solvent (wt. %) | Temp. during the dropwise addition of bromine (°C.) | Temp. during aging (°C.) | Reaction solution (after aging) |
| Comparative Example 10 | 113 | 23 | 20.5 | 20 | 20 | Slurry |

TABLE 5

| | Results of the reaction | | | | | | | |
|---|---|---|---|---|---|---|---|---|
| | Isolated TBA crystals | | | | | | Methyl bromide | |
| | Amount (g) | Purity (wt. %) | Yield (mol %) | Whitenesss | Hydrolyzable bromide (ppm) | Inorganic bromine ions (ppm) | Amount formed (g) | Yield[1] (mol %) |
| Example 14 | 42.6 | 99.6 | 97.5 | 96.1 | 15 | 2 | 0.43 | 1.4 |
| Example 15 | 42.0 | 98.9 | 95.5 | 96.0 | 12 | 3 | 0.27 | 0.9 |
| Example 16 | 42.2 | 99.3 | 96.3 | 95.8 | 25 | 2 | 0.33 | 1.1 |
| Example 17 | 42.4 | 99.4 | 96.9 | 95.7 | 20 | 10 | 0.79 | 2.6 |
| Example 18 | 42.5 | 99.6 | 97.3 | 95.6 | 37 | 11 | 0.89 | 2.9 |
| Example 19 | 42.5 | 98.8 | 96.5 | 95.2 | 17 | 3 | 0.26 | 0.9 |
| Example 20 | 41.9 | 97.4 | 93.8 | 94.7 | 16 | 2 | 0.21 | 0.7 |
| Example 21 | 42.3 | 99.2 | 96.4 | 95.0 | 18 | 7 | 0.58 | 1.9 |
| Comparative Example 7 | 42.3 | 98.8 | 96.1 | 95.8 | 210 | 25 | 1.31 | 4.3 |
| Comparative Example 8 | 42.4 | 99.6 | 97.1 | 96.0 | 238 | 29 | 6.41 | 21.1 |
| Comparative Example 9 | 42.7 | 99.7 | 97.8 | 96.2 | 198 | 15 | 0.85 | 2.8 |
| Comparative Example 10 | 41.7 | 90.5 | 86.7 | 92.1 | 26 | 3 | 0.09 | 0.3 |

We claim:

1. A process for producing tetrabromobisphenol A, which comprises brominating bisphenol A with bromine in methanol, at a temperature of between 0–50° C., wherein the substrate concentration of bisphenol A to methanol is at most 20 wt/vol%.

2. The process according to claim 1, wherein the substrate concentration of bisphenol A to methanol is at most 16 wt/vol%.

3. The process according to claim 1, wherein the substrate concentration of bisphenol A to methanol is from 0.1 to 10 wt/vol%.

4. A process for producing tetrabromobisphenol A which comprises brominating bisphenol A in methanol, wherein the substrate concentration of bisphenol A to methanol is at most 20 wt/vol%, and the bromination is conducted at a temperature of not higher than 25° C.

5. The process according to claim 4, wherein the substrate concentration of bisphenol A to methanol is at most 20 wt/vol%, and the bromination is conducted at a temperature of not higher than 20° C.

6. The process according to claim 4, wherein the substrate concentration of bisphenol A to methanol is at most 16 wt/vol%, and the bromination is conducted at a temperature of not higher than 25° C.

7. The process according to claim 4, wherein the substrate concentration of bisphenol A to methanol is at most 16 wt/vol%, and the bromination is conducted at a temperature of not higher than 20° C.

8. A process for producing tetrabromobisphenol A which comprises brominating bisphenol A in methanol, wherein at least one organic solvent inert to the bromination reaction and insoluble in water is added to methanol in an amount of from 1 to 8% by weight based on the methanol.

9. The process according to claim 8, wherein said at least one organic solvent is added to methanol in an amount of from 3 to 5% by weight based on the methanol.

* * * * *